(12) United States Patent
Melkent et al.

(10) Patent No.: US 10,105,241 B2
(45) Date of Patent: Oct. 23, 2018

(54) SPINAL IMPLANT SYSTEM AND METHOD

(71) Applicant: Warsaw Orthopedic, Inc., Warsaw, IN (US)

(72) Inventors: Anthony J. Melkent, Germantown, TN (US); Thomas E. Drochner, Memphis, TN (US); Richard A. Hynes, Melbourne Beach, FL (US); James P. Duncan, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 351 days.

(21) Appl. No.: 14/978,685

(22) Filed: Dec. 22, 2015

(65) Prior Publication Data

US 2016/0106553 A1 Apr. 21, 2016

Related U.S. Application Data

(62) Division of application No. 14/047,563, filed on Oct. 7, 2013, now Pat. No. 9,283,091.

(51) Int. Cl.
| | |
|---|---|
| *A61F 2/44* | (2006.01) |
| *A61B 17/88* | (2006.01) |
| *A61F 2/46* | (2006.01) |
| *A61F 2/30* | (2006.01) |

(52) U.S. Cl.
CPC ............ *A61F 2/4611* (2013.01); *A61F 2/442* (2013.01); *A61F 2/4455* (2013.01); *A61F 2/4465* (2013.01); *A61F 2002/30387* (2013.01); *A61F 2002/30507* (2013.01); *A61F 2002/30553* (2013.01); *A61F 2002/30578* (2013.01); *A61F 2002/30579* (2013.01); *A61F 2002/4475* (2013.01); *A61F 2220/0016* (2013.01)

(58) Field of Classification Search
CPC ................. A61F 2/4611; A61F 2/4455–2/447
See application file for complete search history.

(56) References Cited

U.S. PATENT DOCUMENTS

| | | | | |
|---|---|---|---|---|
| 5,683,394 A | * | 11/1997 | Rinner | A61F 2/4455 606/247 |
| 6,156,037 A | * | 12/2000 | Lehuec | A61F 2/446 606/247 |
| 6,235,059 B1 | | 5/2001 | Benezech et al. | |
| 6,306,139 B1 | * | 10/2001 | Fuentes | A61B 17/1728 606/295 |
| 7,955,392 B2 | * | 6/2011 | Dewey | A61B 17/7068 606/248 |
| 8,480,747 B2 | | 7/2013 | Melkent et al. | |
| 8,545,562 B1 | * | 10/2013 | Materna | A61F 2/442 623/17.11 |
| 8,652,182 B1 | * | 2/2014 | Walker | A61B 17/7059 606/295 |
| 8,795,367 B2 | * | 8/2014 | Zipnick | A61B 17/32001 623/17.11 |

(Continued)

*Primary Examiner* — Jacqueline Johanas

(57) ABSTRACT

A spinal implant comprises an implant body extending between an anterior surface and a posterior surface. The implant body includes a first vertebral engaging surface and a second vertebral engaging surface. The implant body includes an outer surface that defines an oblique surface. A wall is connectable with the implant body and translatable relative to the oblique surface. Systems and methods are disclosed.

20 Claims, 18 Drawing Sheets

(56) References Cited

U.S. PATENT DOCUMENTS

| | | | |
|---|---|---|---|
| 8,900,310 B2* | 12/2014 | Carlson | A61F 2/446 623/17.16 |
| 9,107,760 B2* | 8/2015 | Walters | A61F 2/442 |
| 2005/0101960 A1 | 5/2005 | Fiere et al. | |
| 2005/0159813 A1* | 7/2005 | Molz, IV | A61F 2/447 623/17.11 |
| 2008/0177390 A1* | 7/2008 | Mitchell | A61F 2/442 623/17.16 |
| 2009/0105831 A1* | 4/2009 | Jones | A61B 17/7059 623/17.16 |
| 2009/0306779 A1 | 12/2009 | Ahn | |
| 2010/0030334 A1* | 2/2010 | Molz, IV | A61F 2/447 623/17.11 |
| 2011/0208311 A1* | 8/2011 | Janowski | A61F 2/4465 623/17.16 |
| 2011/0288645 A1* | 11/2011 | Braddock, Jr. | A61F 2/4425 623/17.16 |
| 2012/0004729 A1* | 1/2012 | Zipnick | A61B 17/32001 623/17.16 |
| 2012/0277865 A1* | 11/2012 | Trieu | A61F 2/442 623/17.16 |
| 2012/0277867 A1* | 11/2012 | Kana | A61F 2/4455 623/17.16 |
| 2012/0277868 A1* | 11/2012 | Walters | A61F 2/442 623/17.16 |
| 2013/0006360 A1* | 1/2013 | Aferzon | A61F 2/446 623/17.16 |
| 2013/0073045 A1* | 3/2013 | Vestgaarden | A61F 2/447 623/17.16 |
| 2013/0166027 A1* | 6/2013 | Bellas | A61F 2/442 623/17.16 |
| 2013/0218276 A1 | 8/2013 | Fiechter et al. | |
| 2013/0238095 A1* | 9/2013 | Pavento | A61B 17/7059 623/17.16 |
| 2014/0180418 A1* | 6/2014 | Janowski | A61F 2/4465 623/17.16 |
| 2015/0025635 A1* | 1/2015 | Laubert | A61F 2/447 623/17.16 |

* cited by examiner

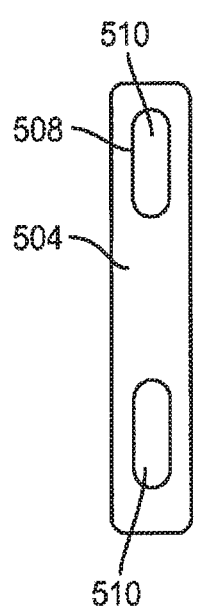
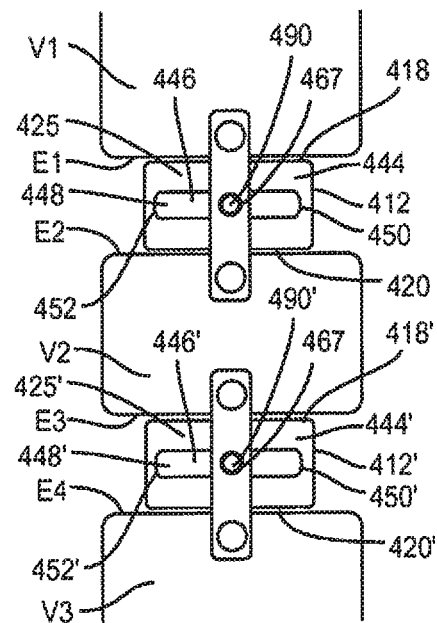
FIG. 28A
FIG. 28B
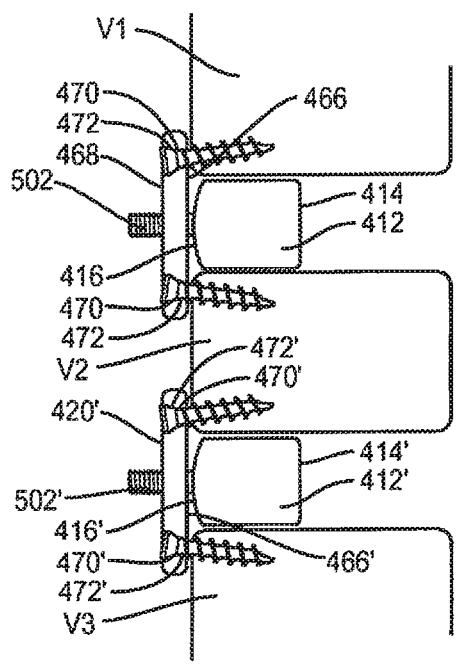
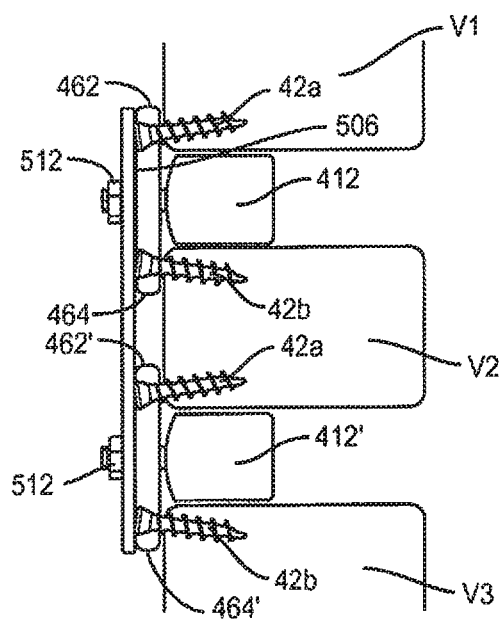
FIG. 28C
FIG. 28D

SPINAL IMPLANT SYSTEM AND METHOD

CROSS-REFERENCE TO RELATED APPLICATIONS

This application is a divisional application of U.S. patent application Ser. No. 14/047,563, filed on Oct. 7, 2013, which is incorporated herein by reference, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Certain spinal surgery approaches utilize a direct lateral approach to access intervertebral spaces, however, these techniques present certain challenges due to the location of musculature and neural structures embedded therein.

This disclosure describes an improvement over these prior art technologies with the provision of specialized instrumentation, implants and techniques to allow for an oblique lateral surgical pathway to the intervertebral spaces.

SUMMARY

A spinal implant comprises an implant body extending between an anterior surface and a posterior surface. The implant body includes a first vertebral engaging surface and a second vertebral engaging surface. The implant body includes an outer surface that defines an oblique surface. A wall or plate is connectable with the implant body and translatable relative to the oblique surface.

BRIEF DESCRIPTION OF THE DRAWINGS

The present disclosure will become more readily apparent from the specific description accompanied by the following drawings, in which:

FIGS. 28A-28D are views of components of one embodiment of a multi-level and connectable system in accordance with the principles of the present disclosure disposed with vertebrae;

DETAILED DESCRIPTION

Figure 1:
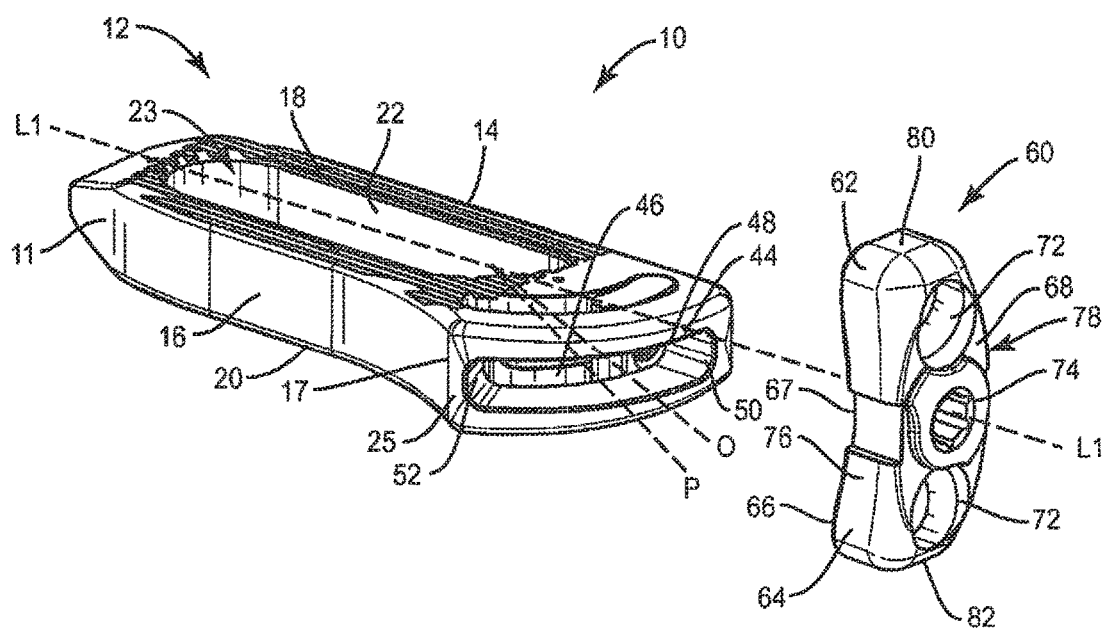
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine, which employ an oblique surgical pathway, which may include an oblique-lateral surgical pathway. In one embodiment, the systems and methods of the present disclosure are employed with a spinal joint and fusion, for example, with a cervical, thoracic, lumbar and/or sacral region of a spine.

In one embodiment, the surgical system includes an interbody implant having an integral floating plate utilized with oblique lateral interbody fusion (OLIF) and direct lateral interbody fusion (DLIF) procedures. In one embodiment, the surgical system includes a standalone interbody implant and a standalone plate configured for connection with each other. In some embodiments, the interbody implant is inserted and moved off oblique into a lateral position and the plate is maintained in the oblique surgical pathway facilitating engagement of screws with vertebrae. In one embodiment, the surgical system includes an interbody implant having a track disposed along an oblique surface of the interbody implant. In one embodiment, the surgical system includes a plate configured for rotation relative to the interbody implant such that a flush or low profile configuration is maintained during insertion. In some embodiments, the plate is configured for rotation in two or more planes such that the plate rotates about a longitudinal axis of the interbody implant. In one embodiment, the plate is configured for rotation about an axis defined by a proximal end of the interbody implant such that the plate rotates into the implant to reduce the profile of the surgical system upon insertion.

In one embodiment, the surgical system includes an interbody implant having a plate freely translatable relative to the interbody implant along an elongated opening, such as, for example, a track. In one embodiment, the surgical system includes an interbody implant having a plate configured to be locked with the interbody implant. In one embodiment, the plate includes a plurality of openings configured to receive fasteners. In one embodiment, the surgical system includes bolts and/or nuts to facilitate translation of the plate relative to the interbody implant. In one embodiment, the surgical system includes fasteners configured to engage the plate in a straight and/or angled configuration.

In one embodiment, the surgical system includes an interbody implant having a plate attached along an oblique surface of the interbody implant. In one embodiment, the surgical system includes an interbody implant having a plate attached along an anterior surface of the interbody implant. In one embodiment, the surgical system includes an interbody implant having a multi-level plate configuration such that single level plates are linked together via an additional plate and locked together. In one embodiment, the surgical system includes an interbody implant having an x-shaped plate configuration such that two separate plates can be inserted in a stacked configuration and rotated and fixed with vertebrae in an x-shaped configuration. In one embodiment, each plate includes a threaded post configured to facilitate attachment of the plates. In some embodiments, the plates are configured to nest within one another to reduce the plate profile. In one embodiment, the plates can be inserted individually into the surgical site.

In one embodiment, the surgical system includes an interbody implant including a track having a constant radii configured to receive a plate. In one embodiment, the surgical system includes an interbody implant including a track having a variable radii configured to receive a plate.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-22, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure, including percutaneous techniques, and mini-open surgical techniques to deliver and introduce instrumentation and/or an implant, such as, for example, an interbody implant, at a surgical site of a patient, which includes, for example, a spine having vertebrae V, as shown in FIGS. 11-22. In some embodiments, a surgical pathway P to a surgical site is formed via an OLIF or DLIF procedure. In some embodiments, the implant can include spinal constructs, such as, for example, bone fasteners, spinal rods, connectors and/or plates.

Figure 11:
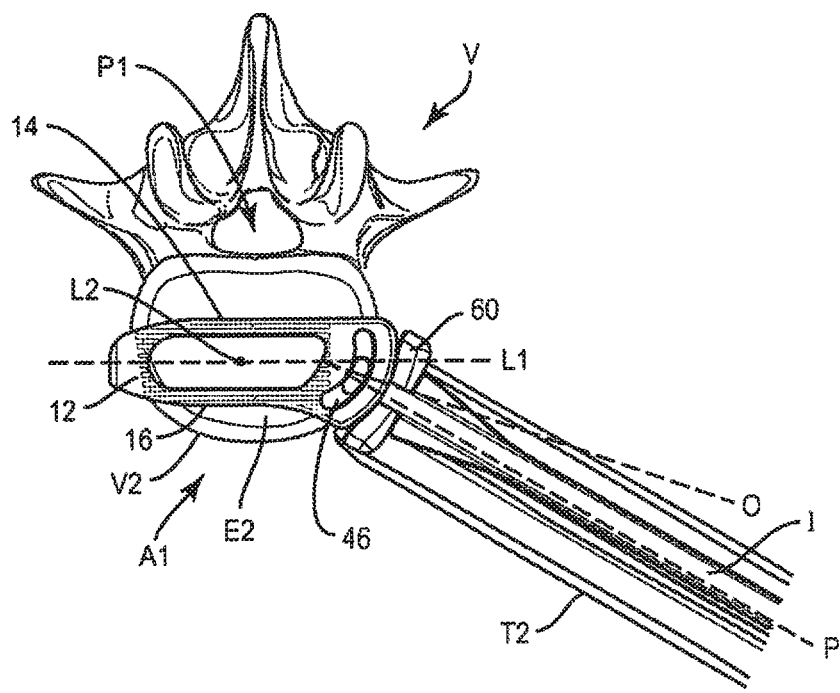
FIG. 11 is a plan view of the components and vertebrae shown in FIG. 10.

Spinal implant system 10 includes an implant body, such as, for example, an interbody cage 12, as shown in FIG. 1. Cage 12 extends between a posterior surface 14 and an anterior surface 16 and defines a longitudinal axis L1. Posterior surface 14 is configured to face a posterior side of a patient body and be disposed adjacent an anterior portion of vertebrae, such as, for example a posterior portion P1 of one or more intervertebral spaces of vertebrae V, as shown in FIG. 11. Anterior surface 16 is configured to face an anterior side of the patient body and be disposed adjacent an anterior portion of vertebrae, such as, for example an anterior portion A1 of one or more intervertebral spaces of vertebrae V, as shown in FIG. 11.

In the various embodiments described herein, cage 12 (and analogous cages described with respect to the various figures) may be provided with a convex distal end 11 (see FIG. 1, showing a "bullet nose") for ease of insertion by the surgeon. Furthermore, as viewed in plan view in FIG. 2, cage 12 may also be provided with chamfers or cut outs 13a, 13b on the distal end such that the cage 12 may be placed in an intervertebral space to avoid impinging on various structures in or near the vertebral body (such as the spinal foramina). Cage 12 may also be provided with a curved end 15 of the posterior surface 14 (immediately opposite the oblique extension 17 described further herein). The curved end 15 may also serve as a cut out to avoid impingement on the spinal foramina or other structures as the cage 12 is placed and/or as the surgeon manipulates the cage 12 along or outside of the surgical pathway P (see FIGS. 12 and 13, for example).

The cage 12 embodiments described herein may also comprise any number and configurations of radiopaque markers (such as tantalum pins, not shown) for visualizing a position of the cage 12 using fluoroscopy during insertion, manipulation and implantation. Such markers may be placed obliquely in the distal end 11, in sidewalls of the cage adjacent the anterior and posterior surfaces (16, 14, respectively), in a proximal end of the implant. Such markers may be placed parallel, oblique to and/or perpendicular to the anterior and posterior surfaces as required to properly visualize the position of the cage 12 relative to the surgical pathway P and/or relative to a preferred oblique axis O to facilitate preferred placement of plate 60 as described further herein.

Figure 13:
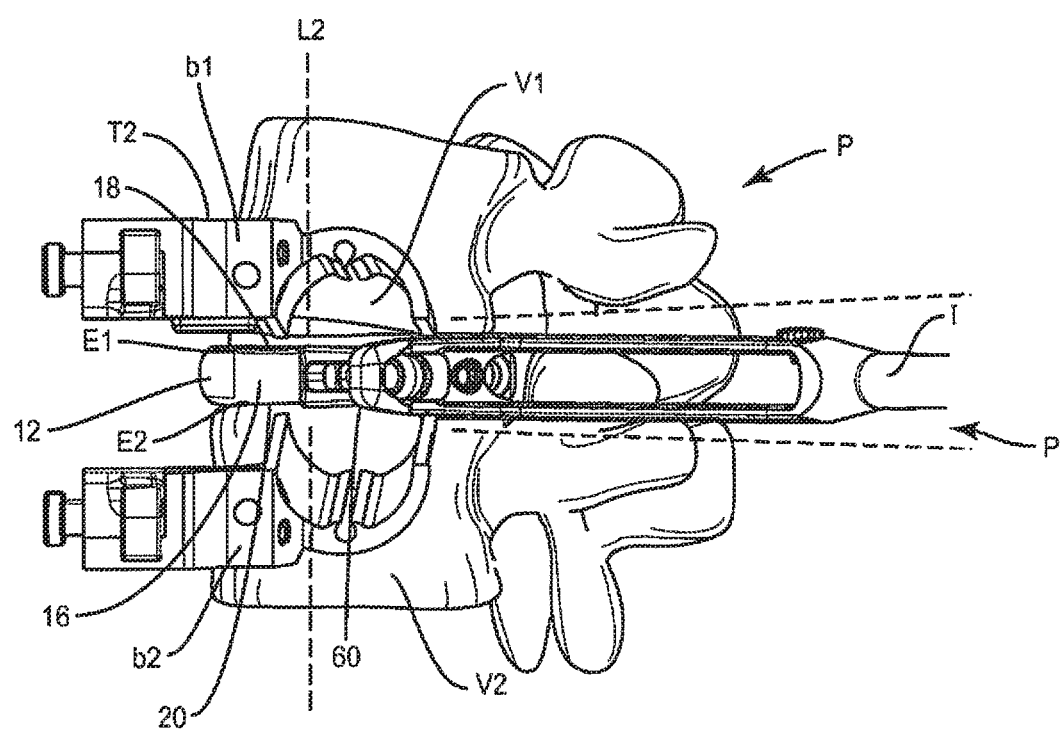
FIG. 13 is a plan view of the components and vertebrae shown in FIG. 10.
Figure 14:
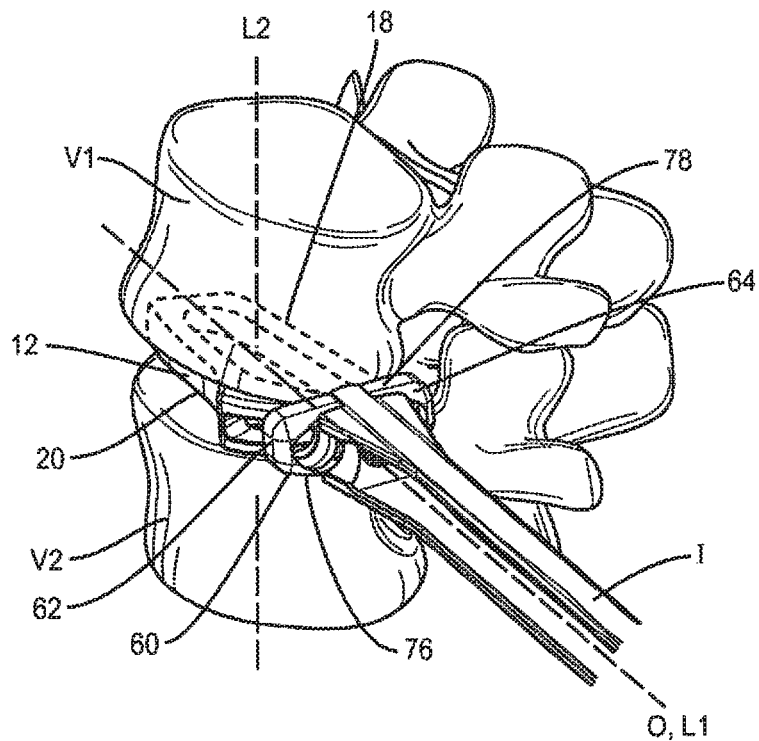
FIG. 14 is a perspective view of components and vertebrae shown in FIG. 10.

Cage 12 includes a first vertebral engaging surface 18 and a second vertebral engaging surface 20. Surfaces 18 may be substantially planar and configured to engage endplate tissue of a vertebral body, such as, for example, an endplate E1 of a V1 vertebral level, as shown in FIG. 13. Surface 20 may be substantially planar and configured to engage endplate tissue of a vertebral body, such as, for example, an endplate E2 of a V2 vertebral level, as shown in FIG. 14. In some embodiments, surfaces 18, 20 may be rough, textured, porous, semi-porous, dimpled, knurled, toothed, grooved and/or polished such that it facilitates engagement with tissue. Surfaces 18, 20 may also be at least partially convex along the longitudinal axis L1 and/or at least partially convex in a direction substantially perpendicular to the longitudinal axis L2 (i.e. from the anterior surface 16 to the posterior surface 14. In some embodiments, surfaces 18, 20 may be angled along the longitudinal axis L1 or angled perpendicular to the longitudinal axis L1 such that anterior surface 16 is taller than posterior surface 14 such that the cage 12 may be capable of creating and/or augmenting lateral or lordotic curvature in a human spine when implanted. In some embodiments, the vertebral tissue may include intervertebral tissue, endplate surfaces and/or cortical bone. In some embodiments, surfaces 18, 20 may be coated with materials suitable for facilitating or encouraging bony ongrowth or fusion including but not limited to titanium and hydroxyapatite (HA) coatings. In embodiments where titanium coatings are applied to surfaces 18, 20, the titanium may be applied in a porous layer using plasma spray technology.

Figure 2:
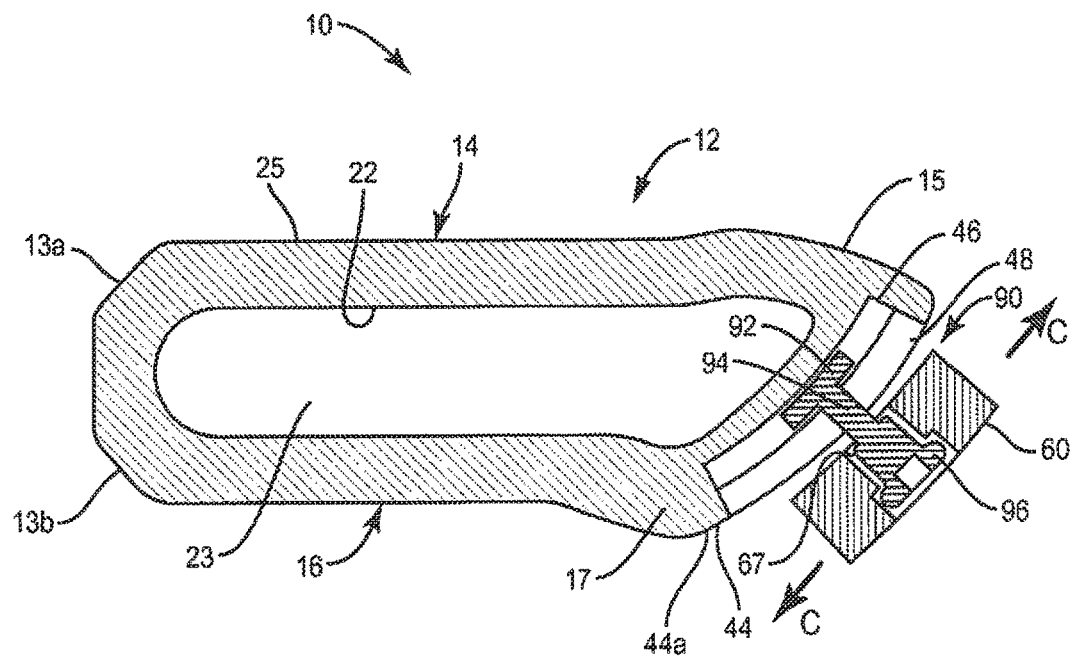
FIG. 2 is a cross section view of the components of the system shown in FIG. 1.

As shown in FIG. 2, Cage 12 may have a substantially rectangular configuration when viewed from above, and includes an inner surface 22 and an outer surface 25. Surface 22 defines an opening 23 configured to receive an agent, which may include bone graft (not shown) and/or other materials, as described herein, for employment in a fixation or fusion treatment. In some embodiments, the plan geometry of cage 12 may have various configurations, such as, for example, oval, round, cylindrical, oblong, triangular, rectangular, polygonal having planar or arcuate side portions, irregular, uniform, non-uniform, consistent, variable, horseshoe shape, U-shape or kidney bean shape (see FIG. 25 for example).

As shown in FIGS. 1 and 2, the cage 12 may comprise a corner extension 17 such that the overall configuration of the cage when viewed from above is substantially asymmetrical about the longitudinal axis L1. Therefore, outer surface 25 at the corner extension 17 (i.e. an extension sidewall 44a, as shown in FIG. 2), may define at least part of an oblique surface 44. The oblique surface 44 defines an elongated opening, such as, for example, a track pathway 48. Oblique surface 44 may extend along the corner extension 17 and proximal end of the cage 12 such that at least a portion of the oblique surface may be in substantial alignment with surgical pathway P, as shown in FIGS. 1 and 2. Track pathway 48 is defined in oblique surface 44 and is in communication with track 46 such that head 92 of connection mechanism 90 may reside substantially in the track 46, and the post 94 of connection mechanism 90 may extend outward through the track pathway 48 to facilitate translation and/or rotation of a wall and/or plate, as discussed further herein. Track pathway 48 In one embodiment, as shown in FIG. 1, pathway 48 extends along an arc that is substantially parallel to the track 46 and to the oblique surface 44. In some embodiments, the track 46, surface 44 and/or track pathway 48 may be arcuate with a single radius defining the arcs. In other embodiments, the track 46, surface 44 and/or track pathway 44 may be arcuate with multiple radii defining one or more of the individual arcs. In one embodiment, oblique surface 44, track 46 (and the accompanying track pathway 48 in communication with track 46) extends along a varying radius of curvature. Track pathway 48 includes a first limit, such as, for example, a lateral axis limit 50, as shown in FIG. 1, and a second limit, such as, for example, an oblique axis limit 52, as shown in FIG. 1. Limits 50, 52 provide a range of translation relative to cage 12 along pathway 48, as discussed herein.

Figure 15:
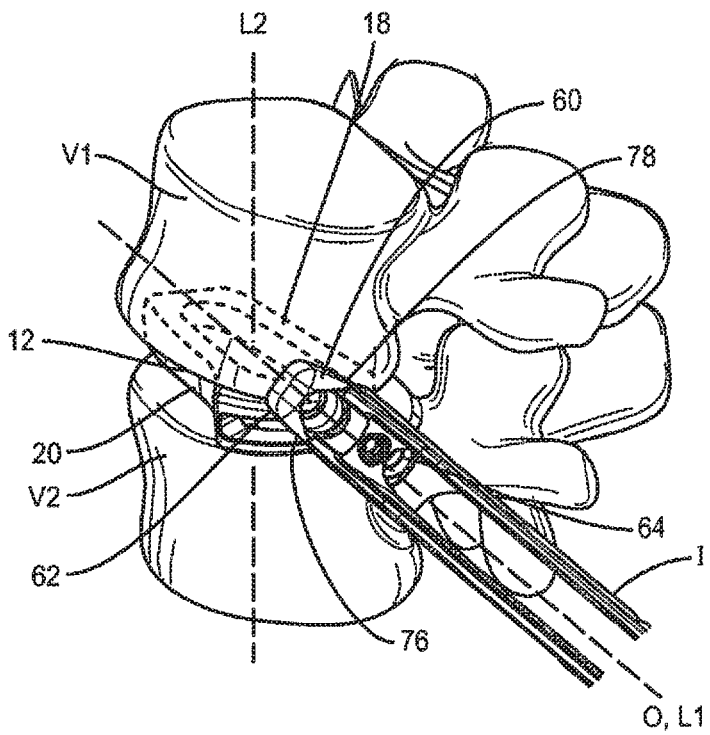
FIG. 15 is a perspective view of the components and vertebrae shown in FIG. 14.
Figure 16:
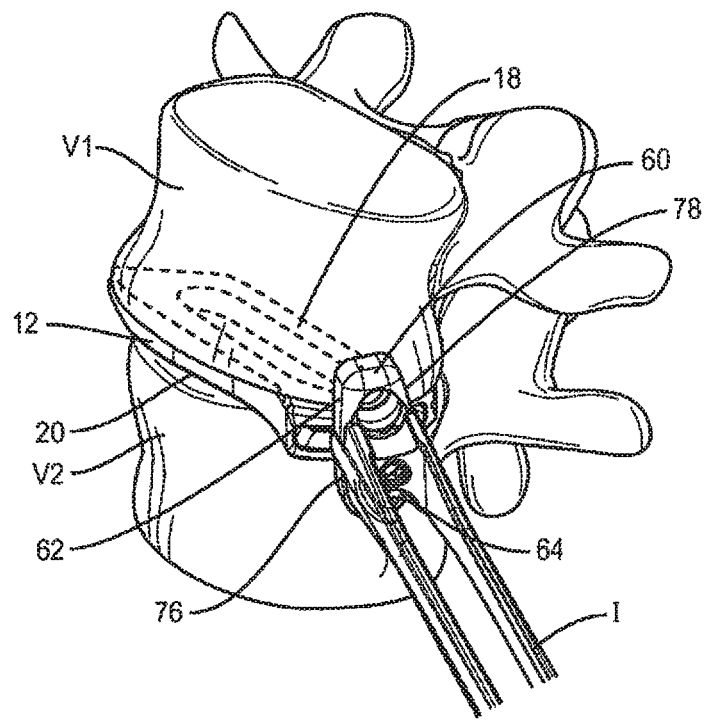
FIG. 16 is a perspective view of the components and vertebrae shown in FIG. 14.

The term "oblique axis" O of the cage 12 body (see element O in FIGS. 1, 11, 12, for example) as used herein may include any axis extending outward from the oblique surface of the cage 12 implant anywhere between the lateral axis limit 50 and the oblique axis limit 52, including but not limited to axes that are co-axial with longitudinal axis L1 and/or the axis defined by surgical pathway P. As shown in FIGS. 14 and 15, at least one of the various oblique axes O defined by the system 10 may be substantially co-axial with the longitudinal axis L1 of cage 12.

In some embodiments, oblique surface 44, track 46 and track pathway 48 may extend along a pathway having various configurations corresponding to the overall shape of the cage 12, such as, for example, round, cylindrical, oblong, triangular, rectangular, polygonal having planar or arcuate side portions, irregular, uniform, non-uniform, consistent, variable, horseshoe shape, U-shape or kidney bean shape. In some embodiments, surface 44 may be rough, textured, porous, semi-porous, dimpled, knurled, toothed, grooved and/or polished such that it facilitates translation. In some embodiments, oblique surface 44 is configured for mating engagement with a surgical instrument, such as, for example, an inserter, which delivers cage 12 adjacent a surgical site via surgical pathway P, as described herein.

Figure 17:
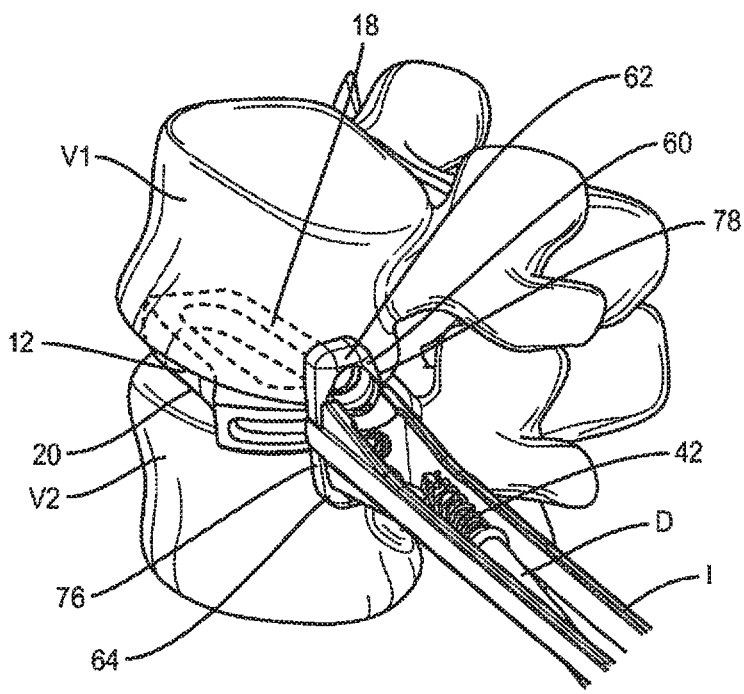
FIG. 17 is a perspective view of components of one embodiment of a system in accordance with the principles of the present disclosure disposed with vertebrae.
Figure 18:
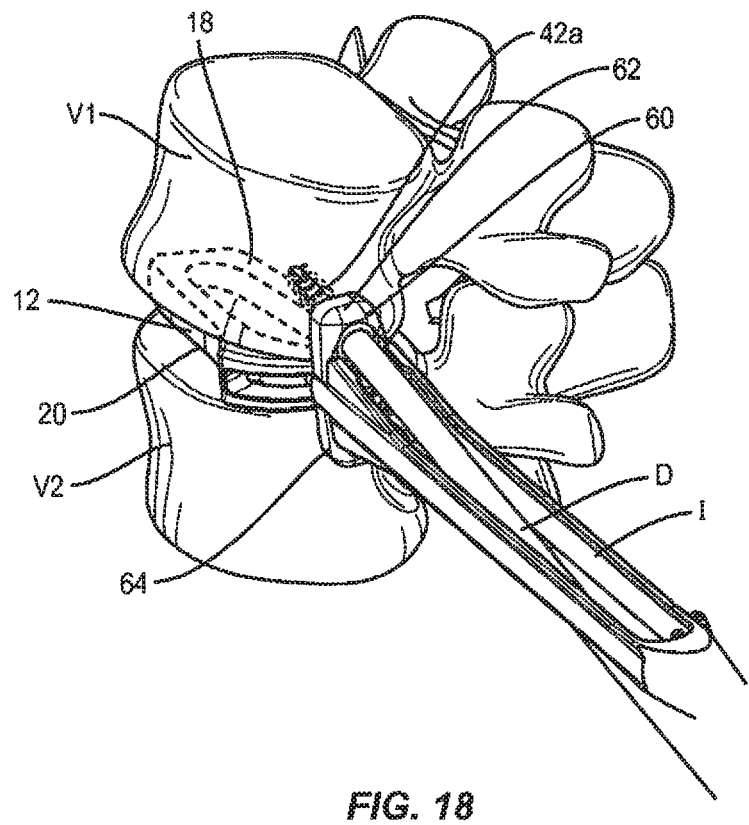
FIG. 18 is a perspective view of the components and vertebrae shown in FIG. 17.

System 10 includes a wall, such as, for example, a plate 60 having a substantially rectangular configuration. In some embodiments, plate 60 can be variously configured, such as, for example, tubular, oval, oblong, triangular, square, polygonal, irregular, uniform, non-uniform, variable, hollow and/or tapered. Plate 60 includes a portion 62 configured to engage a vertebral level V1 and a portion 64 configured to engage a vertebral level V2, as shown in FIG. 17. In one embodiment, plate 60 may be attached with cage 12 prior to implantation or in situ. Plate 60 includes a track engagement surface 66 and an instrument engagement surface 68. Surface 66 defines an opening 67 configured to engage a connection mechanism to facilitate translation along pathway 48. Surface 68 is configured to engage an instrument, such as, for example, an inserter I to facilitate insertion of system 10.

Plate 60 includes an inner surface 70 that defines openings 72 configured to receive fasteners 42, described herein. Openings 72 extend between surface 66 and surface 68. As shown generally in FIG. 25, fasteners 42a are configured for fixation with vertebral level V1 and fasteners 42b are configured for fixation with vertebral level V2. In some embodiments, plate 60 includes a back out prevention element 74, as shown in FIG. 21.

Plate 60 includes a first surface 76 and a second surface 78. Surfaces 76, 78 extend between an end 80 and an end 82. Surfaces 76, 78 may include substantially planar portions that may be initially oriented in a first orientation such that surfaces 76, 78 are substantially in alignment with surfaces 18, 20 along axis L1 in a zero profile alignment with cage 12, as shown generally in FIG. 14. Surfaces 76, 78 may be manipulated to a second orientation, as shown in FIG. 17, such that surfaces 76, 78 are transverse to surfaces 18, 20 and axis L1. FIGS. 14-17 show an exemplary transition of the plate 60 from the first orientation to the second orientation. Plate 60 may also be translatable along track 46 and track pathway 48 about axis L2 of the patient body (defined generally, for example, by a longitudinal axis of the spinal column) and is also rotatable about an oblique axis O of cage 12, as shown in FIG. 15 (with the understanding that the oblique axis O may be, in some configurations substantially co-axial with the longitudinal axis L1). Surface 44 facilitates translation of plate 60 relative to cage 12. This configuration provides selective positioning of plate 60 with respect to a patient's body for adapting to the configuration of the tissue surfaces of vertebrae, as well as provide range of motion limits 50, 52 for plate 60.

Figure 3:
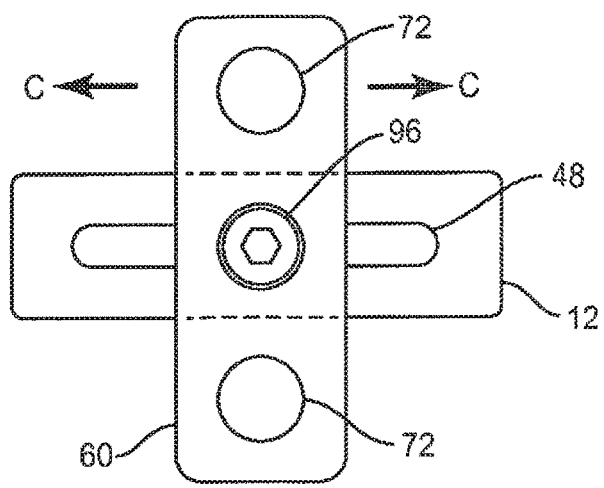
FIG. 3 is an end view of components of the system shown in in FIG. 2.

Surgical system 10 includes a connection mechanism 90 configured to connect plate 60 with track 46. In one embodiment, as shown in FIGS. 2 and 3, mechanism 90 includes a connecting member, such as, for example, a head 92 having an elongated post 94. Head 92 is configured for engagement with and translation along track 46. Post 94 is configured for disposal in opening 67 of plate 60. A nut 96 is configured to lock the head 92 (which may comprise the distal end of a bolt) with plate 60 such that translation of head 92 along track 46 causes plate 60 to translate along surface 44 of cage 12. In some embodiments, a dovetail or t-slot sliding attachment mechanism can be utilized. In some embodiments, plate 60 can be freely translatable in situ within the patient body such that plate 60 is configured for dynamic translation. In some embodiments, plate 60 can be positioned within the patient body and locked into a fixed position.

Figure 21:
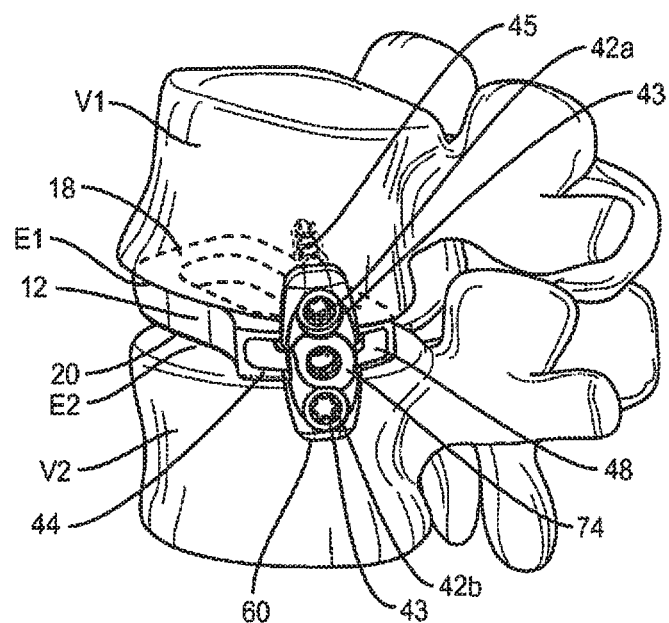
FIG. 21 is a plan view of components and vertebrae shown in FIG. 17.

Spinal implant system 10 includes one or more fasteners 42, such as, for example, as shown in FIG. 21, for attaching plate 60 to bone, as described herein. In some embodiments, fasteners 42a and 42b may be engaged with tissue, such as, for example, the bony structures of a vertebral body in various orientations, such as, for example, series, parallel, offset, staggered and/or alternate vertebral levels. In some embodiments, one or more of fasteners 42 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Fastener 42 comprises a first portion, such as, for example, a head 43 and a second portion, such as, for example, an elongated shaft 45 configured for penetrating tissue. Head 43 includes an engagement portion configured for engagement with a surgical instrument. Shaft 45 has a cylindrical cross section configuration and includes an outer surface having an external thread form. In some embodiments, the external thread form may include a single thread turn or a plurality of discrete threads. In some embodiments, other engaging structures may be located on shaft 45, such as, for example, nail configuration, barbs, expanding elements, raised elements and/or spikes to facilitate engagement of shaft 45 with tissue, such as, for example, vertebrae.

In some embodiments, all or only a portion of shaft 45 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 45 may include one or a plurality of openings. In some embodiments, all or only a portion of the outer surface of shaft 45 may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of shaft 45 may be cannulated.

In some embodiments, system 10 may comprise various surgical instruments, such as, for example, drivers, extenders, reducers, spreaders, distractors, blades, clamps, forceps, elevators and drills, which may be alternately sized and dimensioned, and arranged as a kit. In some embodiments, system 10 may comprise the use of microsurgical and image guided technologies, such as, for example, surgical navigation components employing emitters and sensors, which may be employed to track introduction and/or delivery of the components of system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

Figure 4:
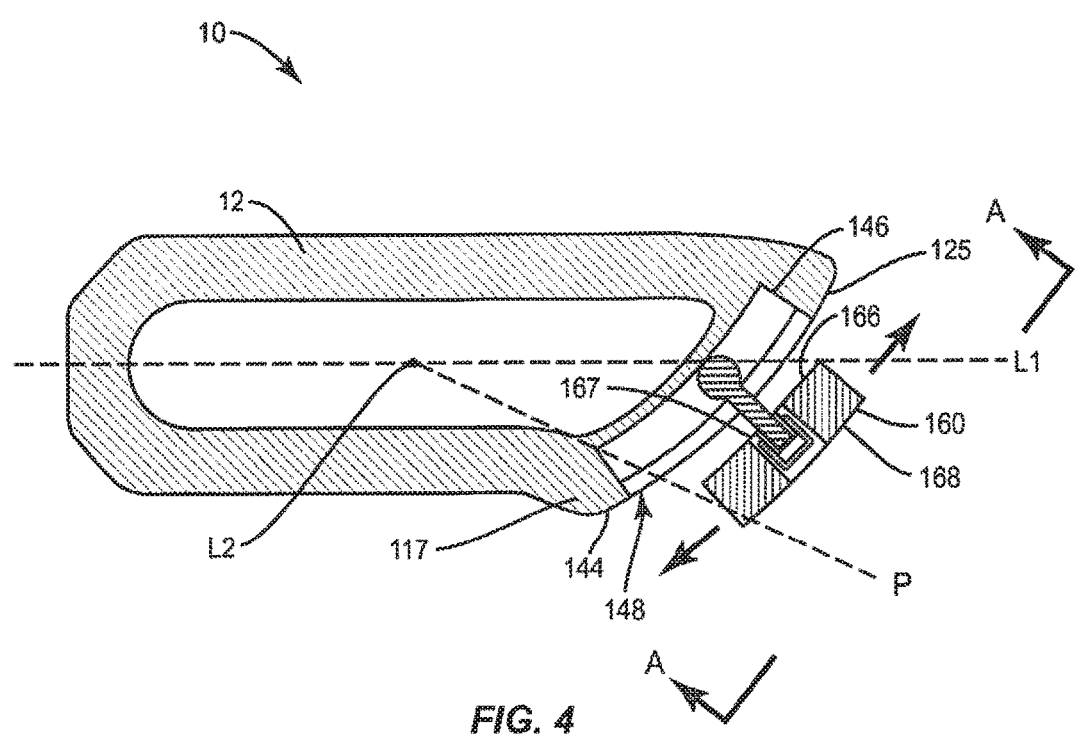
FIG. 4 is a cross section view of components of one embodiment of a system in accordance with the principles of the present disclosure.
Figure 5:
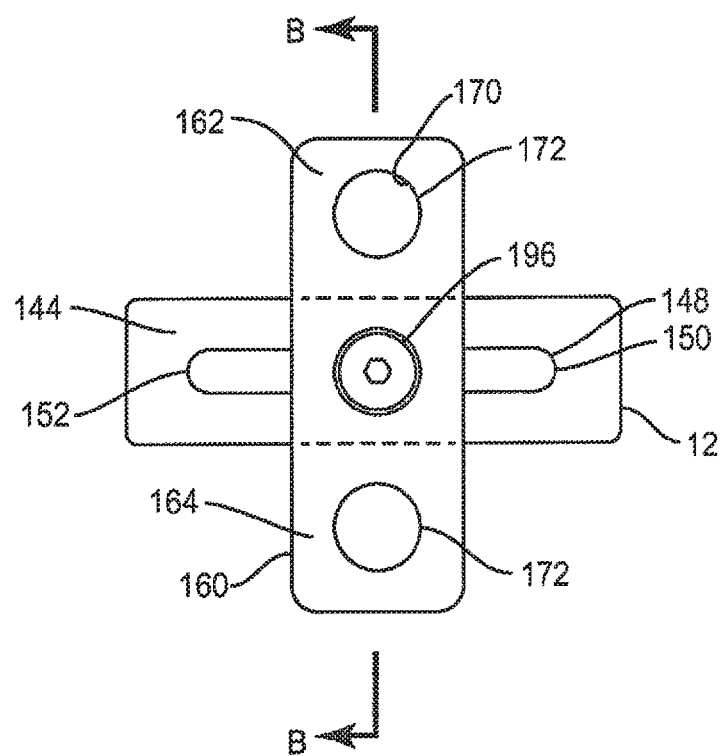
FIG. 5 is an end view taken along lines A-A of components shown in FIG. 4.
Figure 6:
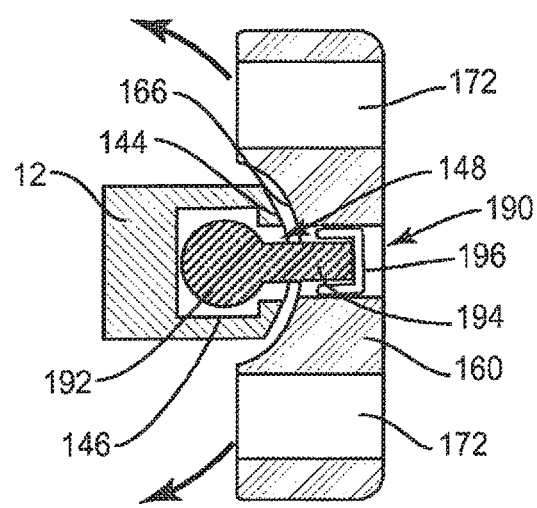
FIG. 6 is a side cross section view taken along lines B-B of components shown in FIG. 5.

In one embodiment, as shown in in FIGS. 4-6, system 10, similar to the systems and methods described herein, comprises a spinal construct including cage 12, described above, and a plate 160, similar to plate 60 described with regard to FIGS. 1-3. Outer surface 125 (or sidewall) of cage 12 includes an oblique surface 144 that defines an elongated opening, such as, for example, a track pathway 148. Oblique surface 144 is oriented with cage 12 and in substantial alignment with surgical pathway P. Track 146 is in open communication with surface 144 to define a track pathway 148 that facilitates engagement with and translation of plate 160. Pathway 148 extends about a longitudinal axis L2 of the patient body (wherein L2 is defined generally by the length of the patient's spine), shown as a point L2 in FIG. 4. Pathway 148 includes a lateral axis limit 150, as shown in FIG. 5, and an oblique axis limit 152, as shown in FIG. 5. Limits 150, 152 provide a range of translation relative to cage 12 along pathway 148, as discussed herein.

Plate 160 includes a portion 162 configured to engage a vertebral level and a portion 164 configured to engage a second vertebral level. Plate 160 includes a track engagement surface 166 and an instrument engagement surface 168. Surface 166 defines an opening 167 configured to engage a connection mechanism to facilitate translation along pathway 148. Surface 168 is configured to engage an instrument to facilitate insertion of system 10. Surface 144 provides range of motion limits 150, 152 for plate 160 for selective positioning of plate 160 to adapt to vertebrae.

Plate 160 includes an inner surface 170 that defines openings 172 configured to receive fasteners 42, described herein. Openings 172 extend between surface 166 and surface 168. A connection mechanism 190 is configured to connect plate 160 with track 146. Mechanism 190 includes a spheroidal joint, such as, for example, a ball screw 192 having an elongated post 194. Screw 192 is configured to provide freedom of movement and/or toggle of plate 160 relative to cage 112. Screw 192 is configured for engagement with and translation along track 146. Post 194 is configured for disposal with opening 167 of plate 160. A nut 196 is configured to lock screw 192 with plate 160 such that translation of screw 192 along track 146 causes plate 160 to translate along surface 144 of cage 12. Screw 192 provides translation and rotation of plate 160 relative to cage 112 in a plurality of axial orientations and in multiple planes. As shown in FIGS. 4 and 6, complementary surfaces 144 and 166 may be arcuate in multiple planes such that the plate 160 may be articulated polyaxially relative to the cage 12.

In assembly, operation and use, as shown in FIGS. 7-22, spinal implant system 10, similar to the systems described herein, is employed with a surgical procedure for treatment of a spinal disorder, such as those described herein, affecting a section of a spine of a patient. System 10 may also be employed with other surgical procedures. To treat the affected section of vertebrae V of a patient utilizing an OLIF and DLIF procedure. In some embodiments, system 10 may include retractors such that no further probe is required. In some embodiments, system 10 may include retractors constrained via frame or semi-constrained using elastic or partial frame.

Figure 10:
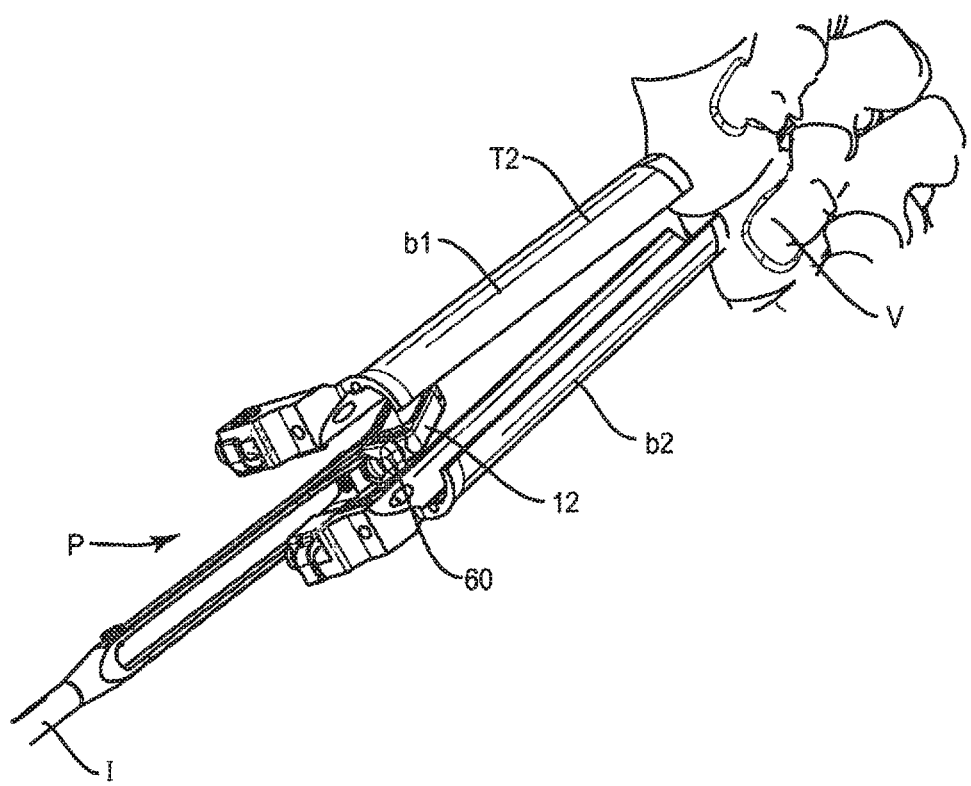
FIG. 10 is a perspective view of components of one embodiment of a system in accordance with the principles of the present disclosure disposed with vertebrae.

In some embodiments, as shown in FIGS. 10-13, a surgical instrument, such as, for example, a retractor T2 is disposed in communication with surgical pathway P for spacing tissue, as shown in FIG. 10. Retractor blades b1, b2 are inserted simultaneously as part of a unitary retractor instrument around one or more intervertebral spaces to protect vessels. The various embodiments of the cage 12 and plate 60 disclosed herein may allow a surgeon to more effectively manipulate the plate 60 and cage 12 construct relative to the retractor T2. For example, as shown in FIGS. 10-13, the inserter I, cage 12, and plate 60 may be inserted along the surgical pathway P substantially between the blades b1, b2 of the retractor T2 with the plate 60 oriented in a low or zero-profile configuration (see FIG. 14, for example). The surgeon may be free to rotate the inserter I (and consequently the cage 12) into position relative to the vertebrae V1 and V2 and outside the extents of the blades b1, b2 (see FIG. 13) with the plate 60 in the low-profile configuration. After positioning the cage 12, the surgeon may then utilize the inserter to rotate the plate 60 into position about the oblique axis O defined by the position of the plate 60 relative to the cage 12 in order to obtain a preferred position of the plate 60 relative to vertebrae V1, V2.

In some embodiments, an annulotomy and/or discectomy is performed with a surgical instrument with x-ray confirmation of the starting point that is central on one or more intervertebral spaces. In some embodiments, system 10 includes a semi-constrained retractor that facilitates minimal tissue pressures on surrounding abdominal structures and provides flexibility such that its blades rotate on a fixed pin allowing greater degrees of freedom of movement and working angles for a practitioner.

A probe is passed into the disc space to secure its location. In one embodiment, the oblique angle and lordotic angle of the probe as it enters the disc space is assessed preoperatively and measured intraoperative using image guidance or using a mechanical or digital protractor. Fluoroscopy, image guidance and/or surgical navigation, as described herein, are used to confirm proper probe alignment into the disc space. In some embodiments, a guide wire is placed through a cannula into the disc space and positioning is confirmed with fluoroscopy. Instruments, such as, for example, a Cobb, mallet, shaver, serrated curettes, rasp, a ring curette, a uterine curette and/or combo tools are utilized to perform a discectomy of the disc space. The instruments enter the patient body obliquely through the retractor and can be turned orthogonally to allow the surgeon to work orthogonally across the disc space. The disc space is distracted until adequate disc space height is obtained.

In some embodiments, a discectomy is performed via surgical pathway P. In some embodiments, trial implants are delivered along surgical pathway P and used to distract one or more intervertebral spaces and apply appropriate tension in the intervertebral space allowing for indirect decompression. In one embodiment, a direct decompression of the disc space is performed by removing a portion of a herniated disc. In some embodiments, the size of cage 12 is selected after trialing, cage 12 is visualized by fluoroscopy and oriented before malleting into intervertebral space. Trialing is utilized to establish a starting point for cage 12 insertion. In some embodiments, an anterior longitudinal ligament (ALL) release procedure can be performed using an OLIF or a DLIF approach post-discectomy. For example, loosening the ALL can be performed by placing holes or partial cuts in the ALL such that the OLIF surgical pathway is immediately closer to the ALL.

Figure 7:
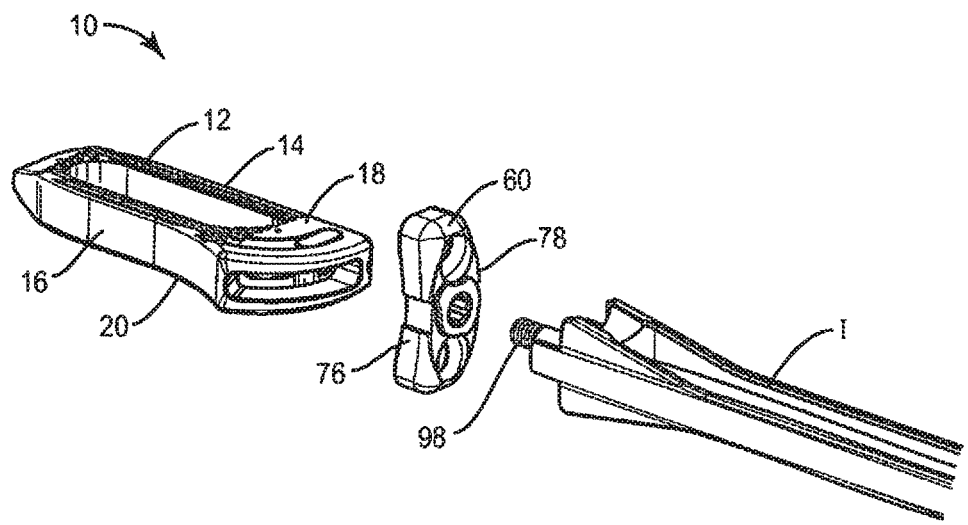
FIG. 7 is a perspective view of components of one embodiment of a system in accordance with the principles of the present disclosure.
Figure 8:
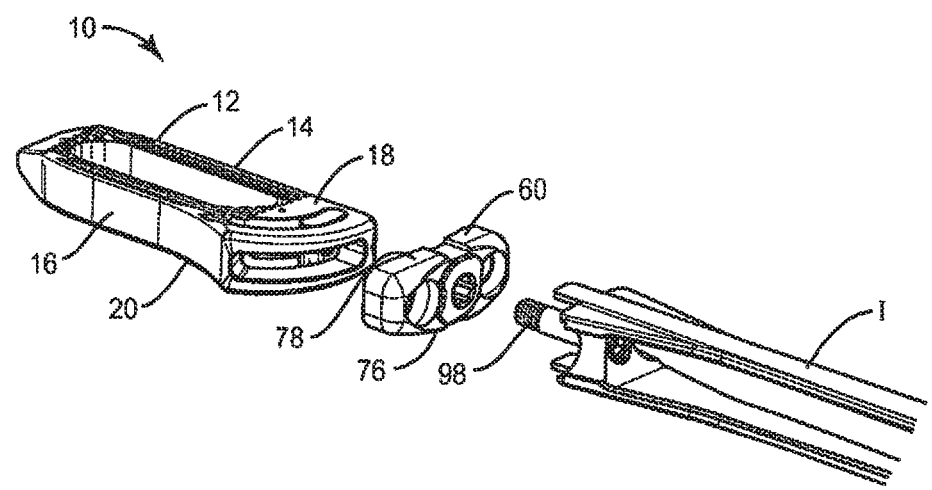
FIG. 8 is a perspective view of the components shown in FIG. 7.
Figure 9:
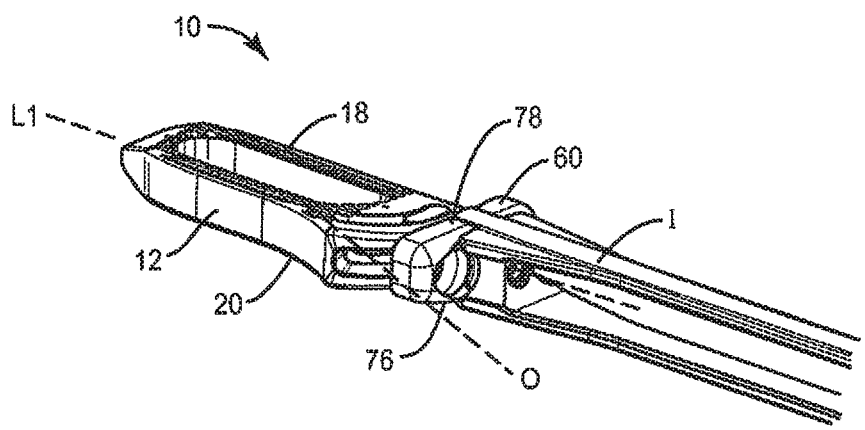
FIG. 9 is a perspective view of the components shown in FIG. 7.

Pilot holes or the like are made in selected vertebra V1, V2 of vertebrae V adjacent the intervertebral space, via surgical pathway P, for receiving bone fasteners 42a, 42b. As shown in FIGS. 7 and 8, inserter I is attached with cage 12 and/or plate 60. Inserter I delivers cage 12 and plate 60 along surgical pathway P adjacent to a surgical site for implantation adjacent the intervertebral space between V1 and V2. In one embodiment, inserter I includes a navigation components to facilitate placement of cage 12 and plate 60 between vertebrae V1, V2. In some embodiments, system 10 may comprise various surgical instruments, such as, for example, drivers, extenders, reducers, spreaders, distractors, blades, clamps, forceps, elevators and drills, which may be alternately sized and dimensioned, and arranged as a kit. In some embodiments, system 10 may comprise various surgical instruments, such as, for example, drivers, extenders, reducers, spreaders, distractors, blades, clamps, forceps, elevators and drills, which may be alternately sized and dimensioned, and arranged as a kit. In some embodiments, system 10 may comprise the use of microsurgical and image guided technologies, such as, for example, surgical navigation components employing emitters and sensors, which may be employed to track introduction and/or delivery of the components of system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

During insertion, plate 60 can be disposed such that surfaces 76, 78 are substantially perpendicular to surface 44 (FIG. 7) or surfaces 76, 78 are substantially aligned with surfaces 18, 20 forming a zero profile implant (FIG. 8). A pivot bolt 98 is utilized to provisionally fix plate 60 and cage 12 with inserter I. Tightening of bolt 98 causes cage 12, plate 60 and inserter I to be drawn together and held in a fixed orientation during insertion. Cage 12 and plate 60 are inserted through retractor T2 adjacent the surgical site. Anterior surface 16 faces an anterior side of the patient body adjacent anterior portion A1 and posterior surface 14 faces a posterior side of the patient body adjacent posterior portion P1, as described herein with respect to FIGS. 11 and 12. Surface 18 engages endplate tissue of endplate E1 and surface 20 engages endplate tissue of endplate E2. In some embodiments, after implantation of cage 12 and plate 60, a practitioner can loosen the connection of inserter I, cage 12 and plate 60. This configuration allows plate 60 to rotate and/or translate relative to cage 12, which provides cage 12 and plate 60 relative freedom of movement such that the practitioner can maneuver the spinal construct for final placement of cage 12 and/or plate 60.

Inserter I is an adaptable instrument configured to perform multiple applications during a surgical procedure. In some embodiments, inserter I can prepare and/or create a cavity in tissue, such as, for example, bone. Inserter I guides a surgical instrument, such as, for example, a drill, tap and/or an awl, as well as guiding fasteners to penetrate tissue. In some embodiments, inserter I is a guide that holds plate 60 and cage 12 together. Surgical instruments including an awl, a tap and screws are passed through inserter I.

Figure 12:
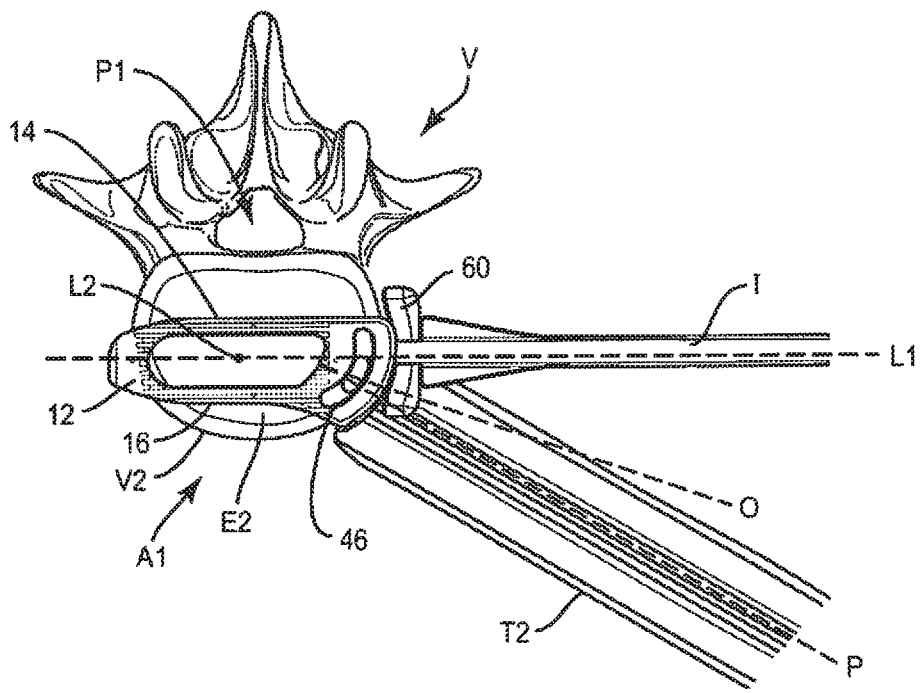
FIG. 12 is a plan view of the components and vertebrae shown in FIG. 10.

In one embodiment, inserter I is utilized to apply a force to plate 60 such that plate 60 is translatable along track 46, as shown by arrows C in FIGS. 2 and 3. In one embodiment, as shown in FIG. 11, plate 60 is positioned at an oblique angle relative to cage 12, prior to rotation of plate 60. In one embodiment, as shown in FIG. 12, plate 60 is translated along track 46 to a position laterally disposed relative to cage 12, prior to rotation and positioning of plate 60. Plate 60 is translated between lateral axis limit 50 and oblique axis limit 52 to facilitate proper positioning of plate 60 relative to cage 12.

Figure 19:
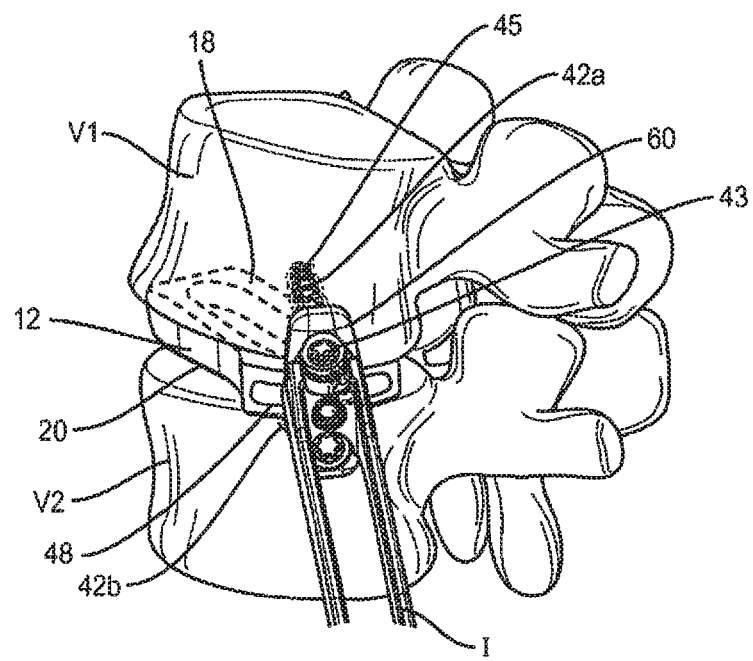
FIG. 19 is a plan view of the components and vertebrae shown in FIG. 17.
Figure 20:
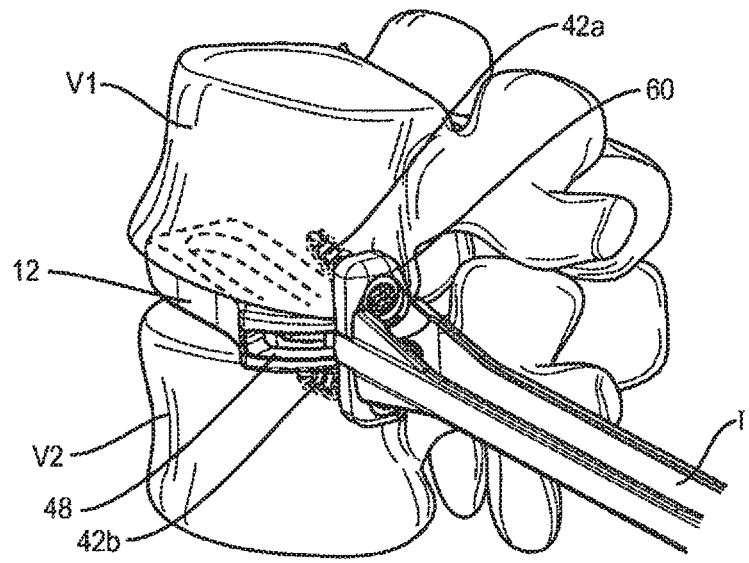
FIG. 20 is a perspective view of the components and vertebrae shown in FIG. 17.
Figure 22:
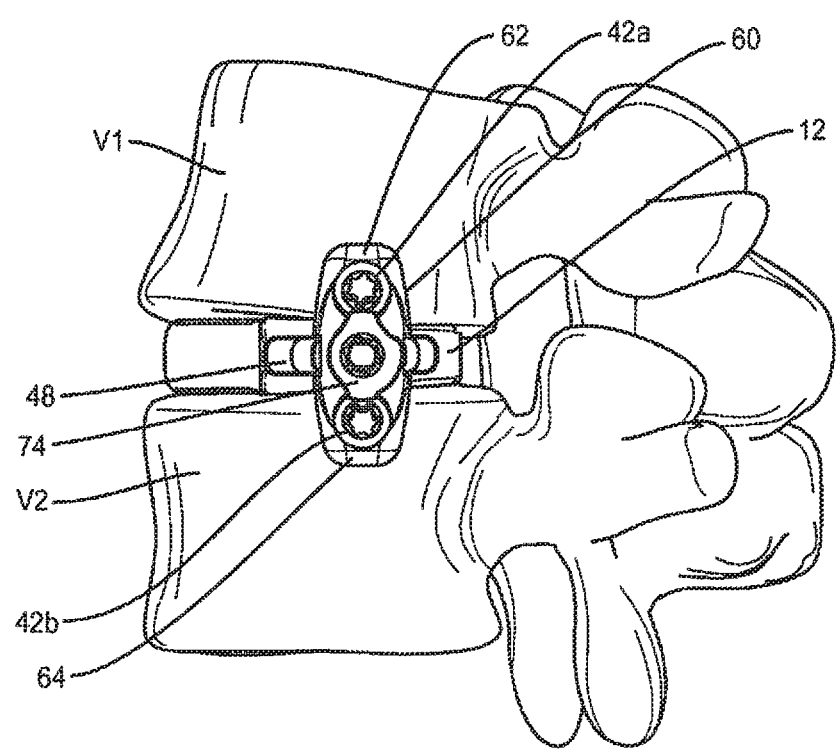
FIG. 22 is a plan view of components and vertebrae shown in FIG. 17.

As shown in FIGS. 14-18, plate 60 is rotated into position such that portion 62 is oriented to engage vertebra V1 and portion 64 is configured to engage vertebra V2. Rotation of plate 60 in situ facilitates insertion due to a low profile configuration of cage 12 and plate 60 during insertion. Translation and rotation of plate 60 allows selective manipulation of plate 60 to facilitate plate 60 adapting with vertebrae. Fasteners 42a, 42b are inserted along inserter I via a driver D through openings 72 such that fastener 42a engages vertebra V1 and fastener 42b engages vertebra V2. Driver D is disposed adjacent the intervertebral space and is manipulated to drive, torque, insert or otherwise connect bone fasteners 42a, 42b adjacent the intervertebral space. In some embodiments, the driver may include surgical navigation components, as described herein, to establish a screw pathway that is substantially concurrent with and/or parallel to the surgical approach angle. In one embodiment, as shown in FIGS. 19 and 21, plate 60 is fixed with fasteners 42a, 42b at an oblique angle relative to cage 12. In one embodiment, as shown in FIG. 20, plate 60 is fixed with fasteners 42a, 42b laterally to cage 12. In one embodiment, as shown in FIG. 22, plate 60 includes a back out prevention element 74 that is rotated to prevent fasteners 42, 42b from disengaging from vertebrae V1, V2.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 23:
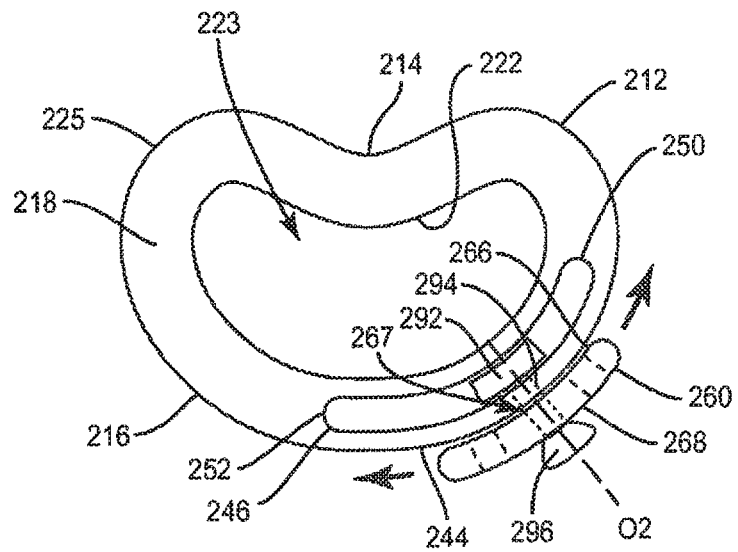
FIG. 23 is a plan view of components of one embodiment of a system in accordance with the principles of the present disclosure.
Figure 24:
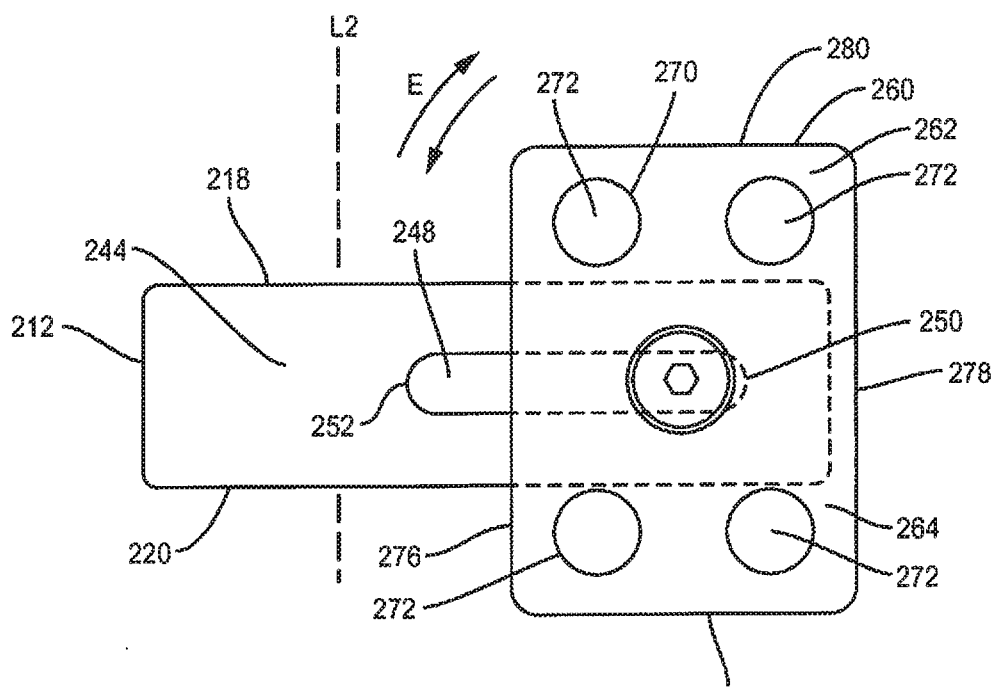
FIG. 24 is a side view of the components shown in FIG. 23.
Figure 25:
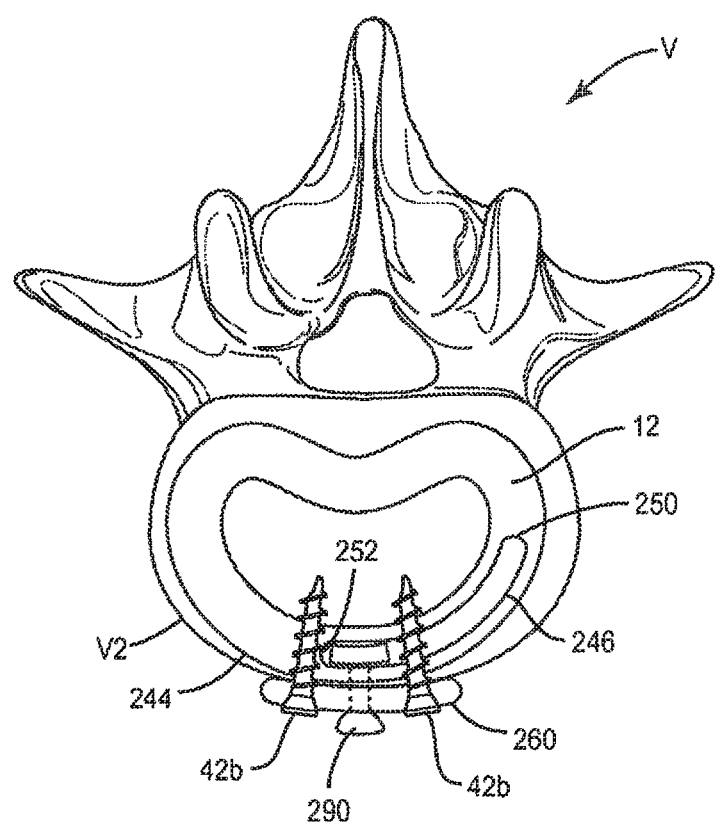
FIG. 25 is a plan view of components of one embodiment of a system in accordance with the principles of the present disclosure.

In one embodiment, as shown in FIGS. 23-25, system 10, similar to the systems and methods described herein, comprises a spinal construct including cage 212, similar to cage 12, described above, and a plate 260, similar to plate 60 described above. Cage 212 extends between a posterior surface 214 and an anterior surface 216. Cage 212 includes a first vertebral engaging surface 218 and a second vertebral engaging surface 220. Surface 218 may be substantially planar and configured to engage endplate tissue of a vertebral body, such as, for example, an endplate of a vertebral level (not shown, but may be immediately caudal to the vertebral body V2 shown in FIG. 25). Surface 220 may be substantially planar and configured to engage endplate tissue of a vertebral body, such as, for example, an endplate E2 of a V2 vertebral level, as shown in FIG. 25. The surfaces 218, 220 may also be provided with convex portions and/or inclined portions to provide for lordotic correction and/or to better conform to the anatomy of particular vertebral endplates.

In the embodiments of FIGS. 23-25, cage 212 has a substantially kidney bean shaped cross section configuration (such as that which may be used in an anterior and/or anterior-oblique spinal approach) and includes an inner surface 222 and an outer surface 225. Surface 222 defines an opening 223 configured to receive an agent, which may include bone graft (not shown) and/or other materials, as described herein, for employment in a fixation or fusion treatment. Outer surface 225 includes an elliptical oblique surface 244 that defines a track 246. Track 246 is in open communication with surface 244 to define a track pathway 248 that facilitates connection with and translation of plate 260. In one embodiment, as shown in FIG. 23, pathway 248 is arcuate in shape. Pathway 248 includes a lateral axis limit 250 and an oblique axis limit 252. Limits 250, 252 provide a range of translation relative to cage 212, as discussed herein.

System 10 includes plate 260 having a substantially rectangular configuration. Plate 260 includes a portion 262 configured to engage a vertebral level V1 and a portion 264 configured to engage a vertebral level V2. Plate 260 includes a track engagement surface 266 and an instrument engagement surface 268. Surface 266 defines an opening 267 configured to engage a connection mechanism 290 to facilitate translation along pathway 248. Surface 268 is configured to engage an inserter (not shown) to facilitate insertion of system 10. As shown in the plan view of FIG. 23, surfaces 266, 268 may be arcuate in shape such that plate 260 conforms to edge 244 of cage 212.

Plate 260 includes an inner surface 270 that defines openings 272 configured to receive fasteners 42, described herein. Openings 272 extend between surface 266 and surface 268. Fasteners 42a (not shown) are configured for fixation with vertebral level V1 and fasteners 42b are configured for fixation with vertebral level V2. In one embodiment, fasteners 42 are aligned to engage vertebrae in a straight orientation. In some embodiments, fasteners 42 are configured to engage vertebrae at an angled orientation.

Plate 260 includes a first surface 276 and a second surface 278. Surfaces 276, 278 extend between an end 280 and an end 282. Plate 260 is translatable, as shown by arrows D in FIG. 23, about pathway 248 about an axis L2 of the patient body and rotatable about surface 244 about an oblique axis O2 of cage 212. The term "oblique axis" O2 (see element O2 in FIG. 23, for example) as used herein may include any axis extending outward from the oblique surface anywhere between the lateral axis limit 250 and the oblique axis limit 252.

As shown in FIG. 23, connection mechanism 290 includes a bolt 292 having an elongated post 294. Bolt 292 is configured for translation along track 246. Post 294 is configured to engage opening 267 of plate 260. A nut 296 is configured to lock bolt 292 with plate 260 such that translation of bolt 292 along track 246 causes plate 260 to translate along surface 244 of cage 212. It should be understood that the positioning of the nut 296 and bolt 292 may be reversed in various embodiments as necessary.

In one embodiment, as shown in FIG. 23, plate 260 is translated along track 246 to a position relative to cage 212, prior to rotation and positioning of plate 260. Plate 260 is translated between lateral axis limit 250 and oblique axis limit 252 to facilitate proper positioning of plate 260 relative to cage 212. Plate 260 is rotated into position as shown by arrows E in FIG. 24, such that portion 262 is oriented to engage vertebra V1 and portion 264 is configured to engage vertebra V2. Rotation of plate 260 in situ facilitates insertion due to a low profile configuration of cage 212 and plate 260 during insertion. Translation and rotation of plate 260 allows selective manipulation of plate 260 to facilitate a proper fit with vertebrae.

Figure 26:
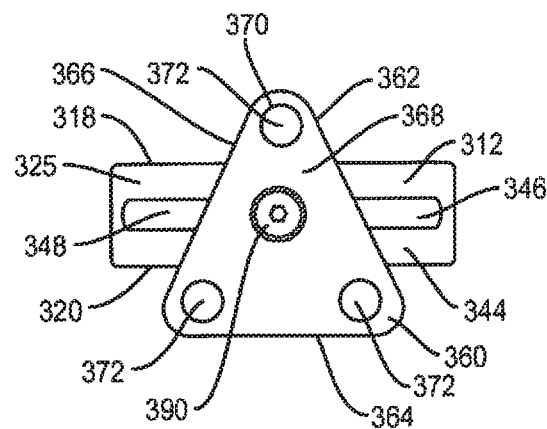
FIG. 26 is a side view of components of one embodiment of a system in accordance with the principles of the present disclosure.
Figure 27:
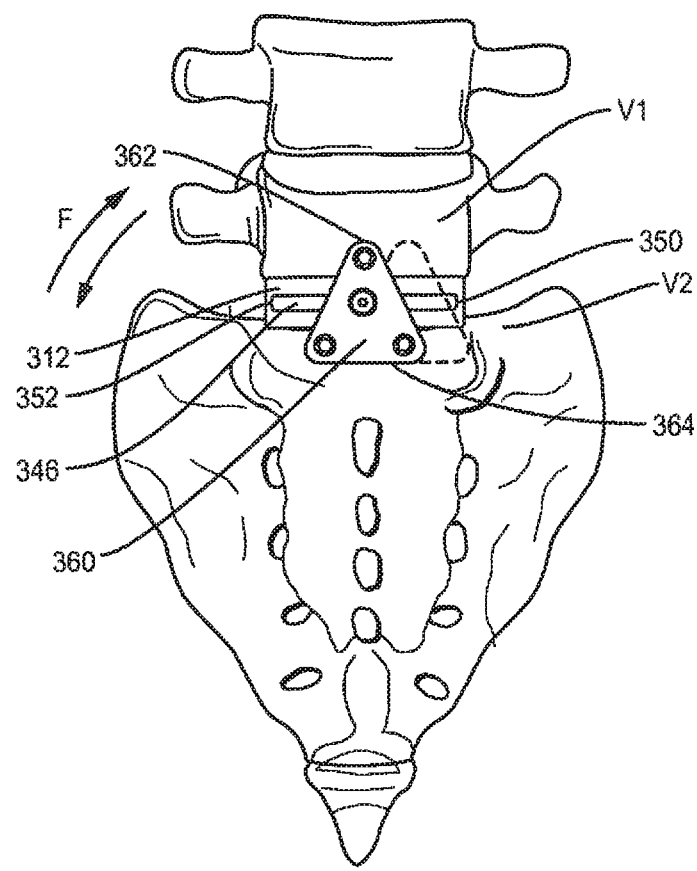
FIG. 27 is a plan view of components shown in FIG. 26 disposed with vertebrae.

In one embodiment, as shown in FIGS. 26-27, system 10, similar to the systems and methods described herein, comprises a spinal construct including cage 312, similar to cage 12, described above, and a plate 360, similar to plate 60 described above. Cage 312 includes a first vertebral engaging surface 318 and a second vertebral engaging surface 320. Surface 318 is substantially planar and configured to engage endplate tissue E1 of a V1 vertebral level, as shown in FIG. 27. Surface 320 is configured to engage endplate tissue E2 of a V2 vertebral level, as shown in FIG. 27. It should be noted that the embodiment of FIGS. 26-27 may be especially useful in lumbo-sacral fusion of the L5-S1 level (wherein V2 is FIG. 27 refers to the sacrum).

Cage 312 may have a substantially rectangular cross section configuration and an outer surface 325. Outer surface 325 includes an arcuate oblique surface 344 that defines a track 346. Track 346 is in open communication with surface 344 to define a track pathway 348 that facilitates engagement with and translation of plate 360.

As shown in FIG. 26, plate 360 includes a substantially triangular configuration. Plate 360 includes a portion 362 configured to engage a vertebral level V1 and a portion 364 configured to engage a vertebral level V2. Plate 360 includes a track engagement surface 366 and an instrument engagement surface 368. Cage 312 and plate 360 are configured to connect with a connection mechanism 390, as discussed herein. Plate 360 includes an inner surface 370 that defines openings 372 configured to receive fasteners 42, not shown. In one embodiment, openings 372 are disposed at angles of approximately 30 degrees relative to plate 360 to facilitate engagement with vertebrae.

In one embodiment, as shown in FIG. 27, plate 360 is translated along track 346 to a position relative to cage 312, prior to rotation and positioning of plate 360. Plate 360 is translated between lateral axis limit 350 and oblique axis limit 352 to facilitate selective positioning of plate 360 relative to cage 312. Plate 360 is rotated into position as shown by arrows F in FIG. 24, such that portion 362 is oriented to engage vertebra V1 and portion 364 is configured to engage vertebra V2. Rotation of plate 360 in situ facilitates insertion due to a low profile configuration of cage 312 and plate 360 during insertion. Translation and rotation of plate 360 allows for selective manipulation of plate 360 to facilitate adaption of plate 360 with vertebrae.

In one embodiment, as shown in FIGS. 28A-28D, system 10, similar to the systems and methods described herein, comprises a spinal construct including cage 412, similar to cage 12, described above, and a plate 460, similar to plate 60 described above. As shown in FIGS. 28A-28D, system 10 includes a multilevel system having cages 412, 412' and plates 460, 460'. Cage 412, 412' extends between a posterior surface 414, 414' and an anterior surface 416, 416'. Cage 412, 412' includes a first vertebral engaging surface 418, 418' and a second vertebral engaging surface 420, 420'. Surface 418, 418' is substantially planar and configured to engage endplates E1, E3. Surface 420, 420' is configured to engage endplates E2, E4.

Cage 412, 412' includes an outer surface 425, 425' having and oblique surface 444, 444' that defines a track 446, 446'. Track 446, 446' is in open communication with surface 444, 444' to define a track pathway 448, 448' that facilitates engagement with and translation of plate 460, 460'. As shown in FIGS. 28A-28D, plate 460, 460' includes a portion 462, 462' configured to engage a vertebral level V1, V2 and a portion 464, 464' configured to engage a second vertebral level V2, V3. Plate 460, 460' includes a track engagement surface 466, 466' and an instrument engagement surface 468, 468'. Surface 466, 466' defines an opening 467, 467' configured to engage connection mechanism 490, 490' to facilitate translation and rotation of plate 460, 460' along pathway 448, 448'.

Plate 460, 460' includes an inner surface 470, 470' that defines openings 472, 474' configured to receive fasteners 42, described herein. Fasteners 42a (not shown) are configured for fixation with a vertebral level V1, V2 and fasteners 42b are configured for fixation with vertebral level V2, V3.

In one embodiment, as shown in FIGS. 28A-28D, plate 460, 460' is translated along track 446 to a position relative to cage 412, prior to rotation and positioning of plate 460, 460'. Plate 460, 460' is translated between lateral axis limit 450, 450' and oblique axis limit 452, 452' to facilitate selective positioning of plate 460, 460' relative to cage 412, 412'. Plate 460, 460' is rotated into position to engage vertebrae. Rotation of plate 460, 460' in situ facilitates insertion due to a low profile configuration of cage 412, 412' and plate 460, 460' during insertion. Translation and rotation of plate 460, 460' allows for selective manipulation of plate 460, 460' to facilitate adaption of plate 460, 460' with vertebrae.

As shown in FIGS. 28A-28D, plate 460, 460' includes a threaded post 502, 502' configured to receive a plate 504. In one embodiment, posts 502, 502' have multi-axial pivoting to facilitate engagement with plate 504. Plate 504 includes an engagement surface 506 and an inner surface 508. Surface 506 is configured to engage plates 460, 460'. In some embodiments, all or only a portion of the surface 506 may have alternate surface configurations, such as, for example, smooth and/or surface configurations to enhance fixation with tissue, such as, for example, rough, arcuate, undulating, porous, semi-porous, dimpled, polished and/or textured to enhance engagement. Surface 508 defines openings 510 configured to receive posts 502, 502'. In one embodiment, openings 510 are elongated to facilitate positioning of plate 504 over posts 502, 502'. Locking nuts 512, 512' are provided to lock plate 504 in a fixed position with plates 460, 460'. Plate 504 is configured to provide stability to system 10 when engaged with vertebrae V.

Figure 29:
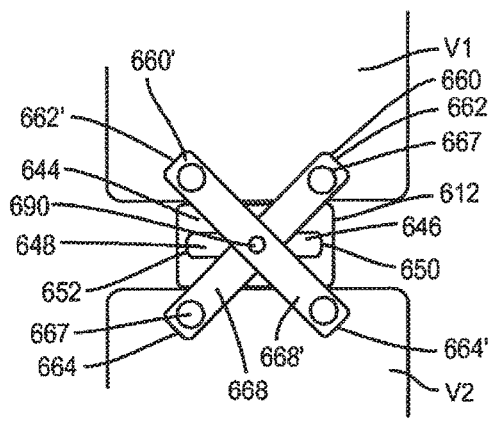
FIG. 29 is a side view of components of one embodiment of a system in accordance with the principles of the present disclosure disposed with vertebrae.
Figure 30:
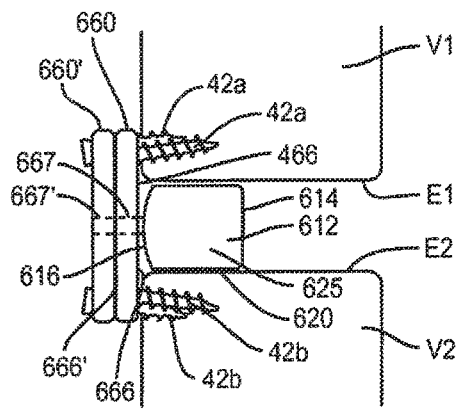
FIG. 30 is a side view of the components and vertebrae shown in FIG. 29.
Figure 31A:
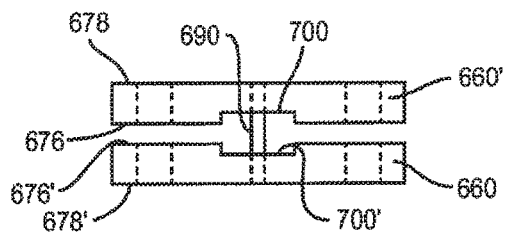
FIGS. 31A-31B are views of components of one embodiment of a system in accordance with the principles of the present disclosure in an unlocked low or zero-profile position.
Figure 32A:
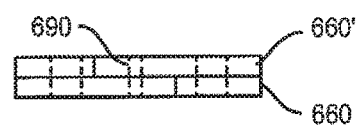
FIG. 32A-32B are views of components shown in FIGS. 31A-31B in a locked transverse position.
Figure 31B:
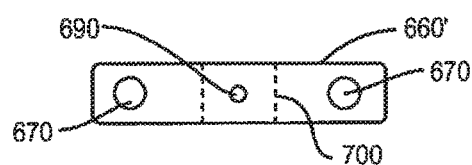
Figure 32B:
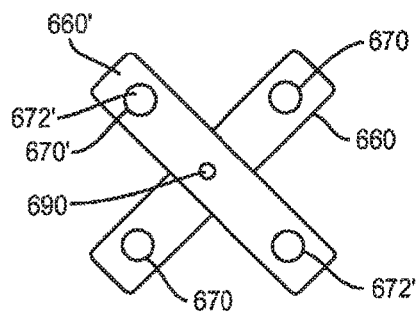

In one embodiment, as shown in FIGS. 29-32, system 10, similar to the systems and methods described herein, comprises a spinal construct including cage 612, similar to cage 12, described above, and a plate 660, similar to plate 60 described above. As shown in FIG. 29, system 10 includes two plates 660, 660'. Cage 612 extends between a posterior surface 614 and an anterior surface 616. Cage 612 includes a first vertebral engaging surface 618 and a second vertebral engaging surface 620. Surface 618 is substantially planar and configured to engage endplate tissue of a vertebral body, such as, for example, an endplate E1 of a V1 vertebral level, as shown in FIG. 30. Surface 620 is configured to engage endplate tissue of a vertebral body, such as, for example, an endplate E2 of a V2 vertebral level, as shown in FIG. 30.

Cage 612 may have a substantially rectangular cross section configuration and includes an outer surface 625. Outer surface 625 includes an arcuate oblique surface 644 that defines a track 646. Track 646 is in open communication with surface 644 to define a track pathway 648 that facilitates translation and rotation of plates 660, 660'. Pathway 648 includes a lateral axis limit 650 and an oblique axis limit 652. Limits 650, 652 provide a range of translation.

As shown in FIG. 29, system 10 includes a first plate 660 and a second plate 660' each having a substantially rectangular configuration. Plate 660, 660' includes a portion 662, 662' configured to engage a vertebral level V1 and a portion 664, 664' configured to engage a vertebral level V2. Plate 660, 660' includes a track engagement surface 666, 666' and an instrument engagement surface 668, 668'. Surface 666, 666' defines an opening 667, 667' configured to engage connection mechanism 690 (hidden) to facilitate translation along pathway 648. Surface 666, 666' define an indent 700, 700' configured to engage each other such that plates 660, 660' are in a nesting configuration upon a cruciate positioning with vertebrae.

Plate 660, 660' includes an inner surface 670, 670' that defines openings 672, 672' configured to receive fasteners 42, described herein. Fasteners 42a are configured for fixation with vertebral level V1 and fasteners 42b are configured for fixation with vertebral level V2.

Plate 660, 660' includes a first surface 676, 676' and a second surface 678, 678'. Upon insertion, plates 660, 660' are collapsed, as shown in FIGS. 31A, 31B and 32A, 32B such that surfaces 676, 676' and 678, 678' are in a parallel orientation forming a low or zero profile plate configuration. Upon insertion, plates 660, 660' are rotated such that surfaces 676, 676' and 678, 678' are positioned in a transverse orientation to engage vertebrae V1, V2. The surfaces 676, 676' may define locking channels 700, 700' that may interact and/or be nested to lock in place when the surfaces 676, 676' and 678, 678' are positioned in a transverse orientation to engage vertebrae V1, V2 (as shown, for example in FIGS. 32A-32B).

In one embodiment, as shown in FIG. 29, plate 660, 660' is translated along track 646 to a position relative to cage 612, prior to rotation and positioning of plate 660, 660'. Plate 660, 660' is translated between lateral axis limit 650, 650' and oblique axis limit 652, 652' to facilitate selective positioning of plate 660, 660' relative to cage 612. Plate 660, 660' is rotated into position to engage vertebrae. Rotation of plate 660, 660' in situ facilitates insertion due to a low profile configuration of cage 612' and plate 660, 660' during insertion. Translation and rotation of plate 660, 660' allows for selective manipulation of plate 660, 660' to facilitate adaption of plate 660, 660' with vertebrae.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising the steps of:
providing a spinal implant including an implant body extending between an anterior surface and a posterior surface, and including an oblique surface;
providing a wall of the spinal implant having a first portion and a second portion;
connecting the wall with the implant body such that the wall is disposed in a zero profile alignment with the implant body;
delivering the spinal implant adjacent a first vertebra and a second vertebra; and
selectively rotating and/or translating the wall relative to the oblique surface such that the first portion is aligned with the first vertebra and the second portion is aligned with the second vertebra,
wherein the oblique surface defines an opening configured for disposal of the wall, the opening defining a range of movement of the wall for the selective translation between a lateral axis and an oblique axis of the implant body.

2. A method as recited in claim 1, wherein selectively rotating and/or translating the wall relative to the oblique surface comprises rotating the wall about a connection mechanism having a head that is disposed in the opening in the oblique surface and a shaft that extends through an opening in the wall.

3. A method as recited in claim 2, wherein the shaft extends through opposite inner and outer surfaces of the wall.

4. A method as recited in claim 2, wherein the head is spheroidal.

5. A method as recited in claim 2, wherein the opening in the oblique surface has an oblong shape.

6. A method as recited in claim 1, further comprising inserting fasteners through holes in the first and second portions and into the first and second vertebrae.

7. A method as recited in claim 6, further comprising rotating a back out prevention element that is rotatable relative to the wall from a first orientation in which arms of the back out prevention element are spaced apart from the fasteners to a second orientation in which the arms overlap the fasteners to prevent the fasteners from backing out of the holes.

8. A method as recited in claim 1, wherein:
connecting the wall with the implant body comprises inserting a head of a connection mechanism into a track in the oblique surface such that a shaft of the connecting member extends through the wall; and
the method further comprises translating the connection member with the head positioned within the track such that the wall moves relative to the implant body and toward the anterior surface.

9. A method as recited in claim 1, wherein:
connecting the wall with the implant body comprises inserting a head of a connection mechanism into a track in the oblique surface such that a shaft of the connecting member extends through the wall; and
the method further comprises translating the connection member with the head positioned within the track such that the plate moves relative to the implant body and toward the posterior surface.

10. A method as recited in claim 1, wherein delivering the spinal implant adjacent to the first and second vertebrae comprises engaging opposite first and second surfaces of the implant body with the first and second vertebrae, the first and second surfaces being angled such that the anterior surface is taller than the posterior surface.

11. A method for treating a spine, the method comprising the steps of:
positioning an implant body of a spinal implant such that top and bottom surfaces of the implant body engage adjacent first and second vertebrae, the implant body extending between an anterior surface and a posterior surface, the implant body including an oblique surface that extends between the anterior and posterior surfaces and between the top and bottom surfaces, the implant body comprising a wall of the spinal implant connected thereto such that axes defined by holes that extend through the plate intersect the implant body; and selectively rotating the wall relative to the oblique surface such that one of the axes intersects the first vertebra and another one of the axes intersects the second vertebra, wherein selectively rotating the wall relative to the oblique surface comprises rotating the wall about a connection mechanism having a spheroidal head that is disposed in an opening in the oblique surface and a shaft that extends through an opening in the wall.

12. A method as recited in claim 11, wherein;

the opening in the oblique surface defines a range of movement of the wall for the selective translation between a lateral axis limit and an oblique axis limit of the implant body; and the method further comprises translating the wall relative to the implant body toward the lateral axis limit.

13. A method as recited in claim 11, wherein:

the opening in the oblique surface defines a range of movement of the wall for the selective translation between a lateral axis limit and an oblique axis limit of the implant body; and the method further comprises translating the wall relative to the implant body toward the oblique axis limit.

14. A method as recited in claim 11, wherein the opening in the oblique surface has an oblong shape.

15. A method as recited in claim 11, further comprising inserting fasteners through holes in first and second portions of the wall and into the first and second vertebrae after selectively rotating the wall relative to the oblique surface.

16. A method as recited in claim 15, further comprising rotating a back out prevention element that is rotatable relative to the wall from a first orientation in which arms of the back out prevention element are spaced apart from the fasteners to a second orientation in which the arms overlap the fasteners to prevent the fasteners from backing out of the holes.

17. A method for treating a spine, the method comprising the steps of:

providing a spinal implant including an implant body extending between an anterior surface and a posterior surface, and including an oblique surface;

providing a wall of the spinal implant having a first portion and a second portion;

connecting the wall with the implant body such that the wall is disposed in a zero profile alignment with the implant body;

delivering the spinal implant adjacent a first vertebra and a second vertebra; and selectively rotating and/or translating the wall relative to the oblique surface such that the first portion is aligned with the first vertebra and the second portion is aligned with the second vertebra, wherein selectively rotating and/or translating the wall relative to the oblique surface comprises rotating the wall about a connection mechanism having a spheroidal head that is disposed in an opening in the oblique surface and a shaft that extends through an opening in the wall.

18. A method as recited in claim 17, wherein the shaft extends through opposite inner and outer surfaces of the wall.

19. A method as recited in claim 17, wherein the opening in the oblique surface has an oblong shape.

20. A method as recited in claim 17, wherein:

the opening in the oblique surface defines a range of movement of the wall for the selective translation between a lateral axis limit and an oblique axis limit of the implant body; and the method further comprises translating the wall relative to the implant body toward the lateral axis limit.

* * * * *

UNITED STATES PATENT AND TRADEMARK OFFICE
CERTIFICATE OF CORRECTION

PATENT NO. : 10,105,241 B2
APPLICATION NO. : 14/978685
DATED : October 23, 2018
INVENTOR(S) : Melkent et al.

It is certified that error appears in the above-identified patent and that said Letters Patent is hereby corrected as shown below:

In the Specification

In Column 1, Line 7, delete "2013," and insert -- 2013, now Pat. No. 9,283,091, --, therefor.

In Column 16, Line 19, delete "openings 472, 474'" and insert -- openings 472, 472' --, therefor.

In the Claims

In Column 19, Line 15, in Claim 12, delete "wherein;" and insert -- wherein: --, therefor.

Signed and Sealed this
Twelfth Day of March, 2019

Andrei Iancu
*Director of the United States Patent and Trademark Office*